US009629875B2

(12) United States Patent
Lentini et al.

(10) Patent No.: US 9,629,875 B2
(45) Date of Patent: Apr. 25, 2017

(54) *CLOSTRIDIUM DIFFICILE* SPORICIDAL COMPOSITIONS

(71) Applicant: Microdermis Corporation, Princeton, NJ (US)

(72) Inventors: Peter J. Lentini, Tarrytown, NY (US); Dawn Lembo, Leonia, NJ (US)

(73) Assignee: Microdermis Corporation, Princeton, NJ (US)

( * ) Notice: Subject to any disclaimer, the term of this patent is extended or adjusted under 35 U.S.C. 154(b) by 0 days.

(21) Appl. No.: 14/683,276

(22) Filed: Apr. 10, 2015

(65) Prior Publication Data

US 2016/0058789 A1  Mar. 3, 2016

Related U.S. Application Data

(60) Provisional application No. 61/978,451, filed on Apr. 11, 2014.

(51) Int. Cl.
*A61K 31/74* (2006.01)
*A61K 33/18* (2006.01)
*A61K 31/194* (2006.01)
*A01N 37/36* (2006.01)
*A01N 59/12* (2006.01)
*A01N 43/36* (2006.01)
*A61K 9/00* (2006.01)
*A61K 31/79* (2006.01)

(52) U.S. Cl.
CPC ............ *A61K 33/18* (2013.01); *A01N 37/36* (2013.01); *A01N 43/36* (2013.01); *A01N 59/12* (2013.01); *A61K 9/0014* (2013.01); *A61K 31/194* (2013.01); *A61K 31/79* (2013.01)

(58) Field of Classification Search
None
See application file for complete search history.

(56) References Cited

U.S. PATENT DOCUMENTS

| 4,271,149 | A | 6/1981 | Winicov et al. |
| 5,665,307 | A | 9/1997 | Kirschner et al. |
| 5,885,620 | A | 3/1999 | Foret |
| 2009/0324737 | A1* | 12/2009 | Walker .................. A61K 8/347 424/616 |

FOREIGN PATENT DOCUMENTS

WO    WO-00/054594 A1    9/2000

OTHER PUBLICATIONS

Kelemen WO 2000/054594 A1, Sep. 2000.*
Gershenfeld, L. and Witlin, B., Iodine as an antiseptic, Ann. NY Acad. Sci., 53(1):172-82 (1950).
International Search Report for PCT/US2015/025259, 3 pages (Jun. 26, 2015).
Written Opinion for PCT/US2015/025259, 8 pages (Jun. 26, 2015).

* cited by examiner

*Primary Examiner* — Robert A Wax
*Assistant Examiner* — Quanglong Truong
(74) *Attorney, Agent, or Firm* — Choate, Hall & Stewart LLP; Brenda Herschbach Jarrell

(57) ABSTRACT

Disclosed are sporicidal compositions, and methods of use thereof. The sporicidal compositions contain water, an organic solvent, and a spore-germinating agent containing an iodide source, a citrate source or both. The compositions have sporicidal activity against, e.g., *Clostridium difficile* spores. The sporicidal compositions can be used alone, or can form part of a disinfecting composition or an antiseptic composition.

17 Claims, 2 Drawing Sheets

CLOSTRIDIUM DIFFICILE SPORICIDAL COMPOSITIONS

BACKGROUND

Spore-forming *Clostridium difficile*-associated diseases (CDAD) remain an important nosocomial infection associated with significant morbidity and mortality. In recent years, the incidence of CDAD has unfortunately increased and high rates of recurrent disease continue with currently available treatment regimens. Typically, *Clostridium difficile* is transmitted by the fecal-oral route. Spores that persist in the environment survive the gastric acid barrier and germinate in the colon. Toxins released from vegetative *C. difficile* cells are responsible for clinical CDAD.

Vegetative *C. difficile* can only survive 15 minutes aerobically, but the bacteria are nonetheless very difficult to eradicate because they form spores. *C. difficile* spores can be found as airborne particles, attached to inanimate surfaces such as hard surfaces and fabrics, and attached to surfaces of living organisims, such as skin and hair. Spores can be found on a patient's skin as well as on any surface in the room that the infected patient occupied. During exams these spores can be transferred to the hands and body of healthcare workers and thereby spread to subsequent equipment and areas they contact.

Hospital discharges for CDAD in the United States doubled between 1996 and 2003. These nosocomial infections are extremely costly to hospitals at $1.28 to $9.55 billion annually in the U.S. alone, mostly due to infected patients requiring extended stays of 3.6 to 14.4 days. Complications of CDAD include life-threatening diarrhea, pseudo-membranous colitis, toxic megacolon, sepsis, and death. Expenses related to treatment of these conditions ranges from $3,669 to $27,290 per patient. CDAD causes death in 1-2% of affected patients.

People are most often infected in hospitals, nursing homes, or institutions, although *C. difficile* infection in the community, outpatient setting is increasing. *C. difficile* infection (CDI) can range in severity from asymptomatic to severe and life-threatening, especially among the elderly. The rate of *C. difficile* acquisition is estimated to be 13% in patients with hospital stays of up to 2 weeks, and 50% in those with hospital stays longer than 4 weeks.

While currently available antibiotics used for treatment of recurrent CDAD lead to symptomatic improvement, they are essentially ineffective against *C. difficile* spores, the transmissible form of the disease. This causes a high risk of relapse occurring post-therapy as sporulated microorganisms begin to germinate. Therefore, controlling *C. difficile* infection requires limiting the spread of spores by good hygiene practices, isolation and barrier precautions, and environmental cleaning.

Because of the prevalence of *C. difficile* in hospitals, healthcare workers and researchers have an interest in developing an agent that can kill *C. difficile* and its spores.

SUMMARY

The present invention encompasses the insight that both citrate and iodide are *C. difficile* germinants, i.e., they facilitate germination of *C. difficile* spores to the vegetative state, where the bacterium is more susceptible to being killed by stressors, such as antimicrobial agents, heat, and air.

DETAILED DESCRIPTION OF CERTAIN EMBODIMENTS

Definitions and Usage

Figure 1:
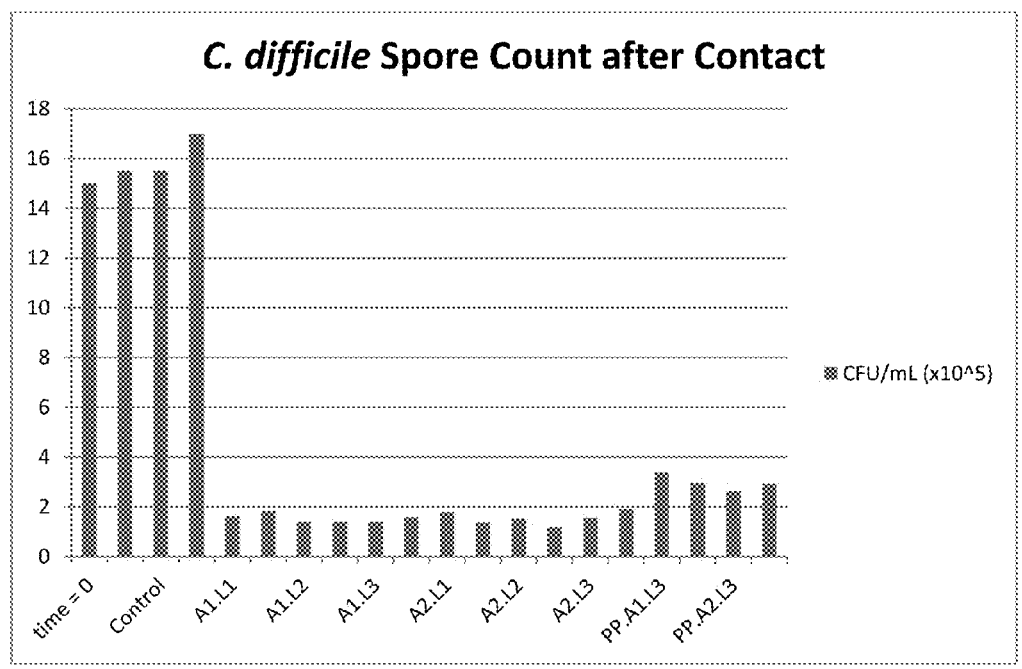
FIG. 1 shows reduction in *C. difficile* spore count after contact with provided compositions according to Example 3.1.

Unless otherwise specified, the word "includes" (or any variation thereon, e.g., "include", "including", etc.) is intended to be open-ended. For example, "A includes 1, 2 and 3" means that A includes but is not limited to 1, 2 and 3.

Unless otherwise specified, the word "about", when used to modify a numeric quantity, means±8% of the numeric value. Thus, "about 5" means 4.6-5.4, "about 70" means 64-76, etc. For this purpose, percentage values are considered as their nominal quantities, e.g., 5% is treated as 5 rather than 0.05. Thus, "about 5%" means 4.6%-5.4%, "about 70%" means 64%-76%, etc.

As used herein, the term "sporicidal" has the meaning ascribed to it in the section labeled "Sporicidal Compositions", below.

*Clostridium difficile* Spores

*Clostridium difficile*, also known as "CDF/cdf" or "*C. diff*", a species of Gram-positive, spore-forming anaerobic bacillus, can lead to severe complications ranging from antibiotic-associated diarrhea (AAD) to severe life-threatening pseudomembranous colitis, a severe infection of the colon. In fact, *C. difficile* is the cause of approximately 25% of all cases of antibiotic-associated diarrhea. Most cases of *C. difficile*-associated disease (CDAD) occur in hospitals or long-term care facilities causing more than 300,000 cases per year in the United States alone. The total US hospital costs for CDAD management have been estimated to be $3.2 billion per year.

Clostridia are motile bacteria that are ubiquitous in nature and are especially prevalent in soil. Under microscopy, clostridia appear as long drumstick-like irregularly-shaped cells with a bulge at their terminal ends. *Clostridium difficile* cells show optimum growth on blood agar at human body temperatures in the absence of oxygen. When stressed, the bacteria produce spores, which tolerate extreme conditions that the active bacteria cannot tolerate.

In small numbers, *C. difficile* do not result in significant disease. The first step in development of *C. difficile* colonization is the disruption of the normal flora of the colon, usually by antibiotics. Antibotic treatments, especially those with a broad spectrum of activity, cause disruption, often resulting from eradication of the normal intestinal flora by antibiotics of normal intestinal flora, leading to an overgrowth of *C. difficile*. *C. difficile* is currently the most common cause of nosocomial diarrhea with significant morbidity and mortality. The *C. difficile* bacteria, which naturally reside in the human intestines, overpopulate and release toxins that can cause bloating, constipation, or diarrhea with abdominal pain, which may become severe. Latent symptoms often mimic some flu-like symptoms.

Antibiotic treatment of *C. difficile* infections can be difficult, due both to antibiotic resistance as well as physiological factors of the bacteria itself. Because the organism forms acid- and heat-resistant spores, *C. difficile* spores can persist in the environment for years, and contamination by *C. difficile* is very common in hospital, clinical, long-term care or nursing home environments. Often, it can be cultured from almost any surface in a hospital. Patient-to-patient transmission of *C. difficile* spores occurs by sharing medical equipment or facilities in hospitals, nursing homes and other extended-care facilities. Typically, *C. difficile* is transmitted from person to person by the fecal-oral route. Ingested spores of *C. difficile* survive the gastric acid barrier and germinate in the colon. Vegetative cells release two potent toxins that ultimately mediate diarrhea and colitis.

Given the pathogenesis of *C. difficile*, judicious use of antibiotics and strict infection control and environmental measures are keys to the prevention of disease. The implementation of antibiotic stewardship programs has been associated with decreased incidence of CDAD. To prevent spread of spores, environmental cleaning and patient isolation are needed. Several disinfectants commonly used in hospitals may be ineffective against *C. difficile* spores, and may actually promote spore formation.

*C. difficile* spores are resistant to killing by alcohol-based hand hygiene products and by antimicrobial soaps that are commonly used in healthcare facilities. M. M. Nerandzic and C. J. Donskey (2010), "Triggering Germination Represents a Novel Strategy to Enhance Killing of *Clostridium difficile* Spores", *PLoS ONE* 5(8):e12285, 1-8 ("Nerandzic et al.") (citing K. J. Popovich et al. (2009), *Infect. Control Hosp. Epidemiol.* 30: 959-63). *C. difficile* spores survive for months on surfaces and are resistant to killing by many commonly used disinfectants. Nerandzic et al. (citing D. N. Gerding et al. (2008), *Clin. Infect. Dis.* 46: S43-49). Moreover, low levels of some disinfectants may actually promote increased sporulation by *C. difficile*. Nerandzic et al. (citing W. N. Fawley et al. (2007), *Infect. Control Hosp. Epidemiol.* 28: 920-25; M. H. Wilcox and W. N. Fawley (2000), *Lancet* 356: 1324). Sodium hypochlorite (bleach) is a disinfectant with sporicidal activity, but it has several disadvantages, including being corrosive to many materials, irritating to some patients and staff members, and dependent on correct application by housekeepers. Nerandzic et al. (citing F. Barbut F et al. (2009), *Infect. Control Hosp. Epidemiol.* 30: 507-14.). There is a need to develop a disinfectant that is nonreactive to untargeted materials and nonharmful to humans and environment.

Spore-Germinating Agents

Spore germination, the irreversible loss of spore-specific properties, is an essential step required prior to outgrowth of vegetative cells. Because germinated spores become more susceptible to killing by other stressors, induction of germination is a strategy to facilitate eradication of *C. difficile* spores. See, e.g., M. M. Nerandzic and C. J. Donskey (2010), "Triggering Germination Represents a Novel Strategy to Enhance Killing of *Clostridium difficile* Spores", *PLoS ONE* 5(8):e12285, 1-8 ("Nerandzic et al."). Nerandzic et al. report testing triggering germination as a strategy to enhance UV-C-induced killing of *C. difficile* spores on surfaces, thereby reducing the time and radiation dose necessary for disinfection of hospital rooms with the UV-C device. In addition, Nerandzic et al. report evaluating the potential for initiation of germination to enhance killing of *C. difficile* spores by heat, alcohol, and exposure to room air.

Nerandzic et al. report the following aqueous formulation as a *C. difficile* spore-germination solution: histidine (100 mg/L), tryptophan (100 mg/L), glycine (100 mg/L), tyrosine (100 mg/L), arginine (200 mg/L), phenylalanine (200 mg/L), methionine (200 mg/L), threonine (200 mg/L), alanine (200 mg/L), lysine (300 mg/L), serine (300 mg/L), valine (300 mg/L), isoleucine (300 mg/L), aspartic acid (300 mg/L), leucine (400 mg/L), cysteine (500 mg/L), proline (600 mg/L), glutamic acid (900 mg/L), $KH_2PO_4$ (300 mg/L), $Na_2HPO_4$ (1500 mg/L), NaCl (90 mg/L), $CaCl_2.2H_2O$ (26 mg/L), $MgCl_2.6H_2O$ (20 mg/L), $MnCl_2.4H_2O$ (10 mg/L), $(NH_4)_2SO_4$ (40 mg/L), $FeSO_4.7H_2O$ (4 mg/L), $CoCl_2.6H_2O$ (1 mg/L), $NaHCO_3$ (5000 mg/L) and taurocholic acid (1000 mg/L). However, the authors note that one limitation of their study is that it is not known which components of the solution are essential to stimulate germination to a stage in which enhanced killing by stressors such as UV-C are possible. Among other things, the present invention encompasses the recognition of the source of a problem with the Nerandzic solution. To be practical, or economical, or both, a spore-germinating composition should contain fewer components than the 18 amino acids, 10 minerals and one bile salt of the Nerandzic solution.

In a similar vein, Hoffman (U.S. Patent Application Publication No. 2011/0135702) reports the following as *C. difficile* spore-germinating agents: sodium taurocholate, glycocholate, cholate, glycine and combinations thereof. Hoffman notes that based on the reported experiments, antimicrobial agents alone or in combination with a surfactant had little effect on inactivating *C. difficile* spores, but that sporicidal efficacy was seen when in combination with one or more spore-germinating agents. In the context of the present invention, it is noteworthy that relatively small reductions were seen for the spore-germinating agents alone.

Walker (U.S. Pat. No. 7,192,601) reports a composition having an antibacterial agent and a "spore coat opener". Walker lists the following as an antibacterial agent: a quaternary ammonium compound, a phenolic compound, a monohydric alcohol, hydrogen peroxide, iodine, triclocarban, triclosan, and combinations of these. As a spore coat opener Walker lists an amino acid, a metal chelation agent, a reducing agent or an emulsifier, a surface-active agent, and combinations of these, with examples such as "amino acid mixture", L-alanine, calcium dipicolinate, disodium EDTA, quinone, proanthocyanidin and "reducing agent".

Walker reports the results of various spore-inactivating compositions on *Bacillus subtilis* vs. exposure time. The spore-coat opener (in the compositions that contain a spore-coat opener) is reported to be L-alanine. In addition to the sporicidal compositions, Walker also reports a colony-forming unit (CFU) relative count for compositions containing 0.1% L-alanine in the absence of sporicidal agents. In the context of the present invention, it is noteworthy that an increase in CFU count—to 116% after 4 hours—was reported for the spore-coat opener alone.

Notwithstanding these reports, Worthington (U.S. Patent Application Publication No. 2013/0142856) reports that this "germinate/exterminate" approach has had limited success in the clinical setting. It reports in particular that attempts have been made in the literature to design antibacterial solutions which stimulate germination and which have an antibacterial agent to attack the germinated pathogens, but that the antibacterial agents used in such approaches have an inhibitory effect on the germinating solution.

Sporicidal Compositions

Provided are sporicidal compositions containing water, an organic solvent, and a spore-germinating agent, as further defined herein. As used herein, the term "sporicidal" refers to the ability to reduce the number of spores in a given area. In this sense, it is irrelevant whether a provided composition is able to kill a bacterium in its spore form, or, as is believed, it is able to facilitate germination of a spore to the vegetative state where the bacterium is more susceptible to being killed by stressors (such as air, antimicrobial agents, etc.). Accordingly, as used herein, the term "sporicidal" is meant to be understood by reference to an observable effect rather than to a mechanism of action. Such compositions are useful, for example, for reducing the count of *Clostridium* spores, particularly *Clostridium difficile* spores, on living tissue surfaces (e.g., skin) and/or on non-living tissue surfaces. In some embodiments, provided compositions reduce *Clostridium* spore counts on or in an environmental site. Among other things, in some embodiments, such compositions reduce the likelihood of infection or the spread of infection from the spore-forming bacteria.

As shown in Example 3.1, in some embodiments, provided compositions exhibit sporicidal activity even in the absence of antimicrobial agents. Without wishing to be bound by theory, it is believed that the citrate and iodide sources facilitate germination of *C. difficile* spores to the vegetative state, where the bacterium is more susceptible to being killed by stressors, including air. As described in this Example, spore count reductions of about 88% to about 92% were seen after 8 minutes with compositions of water, propylene glycol and sodium citrate (A1 compositions) or potassium iodide (A2 compositions). Similarly, provided compositions formulated such that they are suitable for topical administration (PP compositions) showed spore count reductions of 78% to about 84% after 8 minutes.

As shown in Example 3.2, in some embodiments, provided compositions containing antimicrobial agents similarly exhibit sporicidal activity. Without wishing to be bound by theory, it is believed that the citrate and iodide sources facilitate germination of *C. difficile* spores to the vegetative state, where the bacterium is more susceptible to being killed by stressors, including antimicrobial agents. However, contrary to the limited success of this germinate/exterminate approach reported by Worthington, provided compositions containing antimicrobial agents exhibit more pronounced sporicidal activity than those without. Thus, spore count reductions of about 99% to about 100% are seen after 1 minute, and remain at about 100% after 10 minutes, with compositions containing 10% PVP-I.

Spore-Germinating Agents: Citrate Source.

In some embodiments, provided compositions include a spore germinating agent that is or includes a citrate source. Because citric acid, $C(OH)(CH_2CO_2H)_2CO_2H$, is a triprotic weak acid, in aqueous solution it exists as a mixture of citrate species: $H_3C_6H_5O_7$, $H_2C_6H_5O_7^-$, $HC_6H_5O_7^{2-}$ and $C_6H_5O_7^{3-}$. As used herein, a "citrate source" is any chemical species that produces or exists at least in part as citric acid and/or one or more citrate ions in aqueous solution. Examples of citrate sources include citric acid, sodium citrate monobasic, sodium citrate dibasic, sodium citrate tribasic, potassium citrate monobasic, potassium citrate dibasic, potassium citrate tribasic, magnesium citrate, magnesium citrate tribasic, calcium citrate tribasic (tricalcium dicitrate), silver citrate (citric acid trisilver salt) and silver dihydrogen citrate, including anhydrous forms and hydrates (both of which are intended at every mention herein unless otherwise specified). As used herein, "sodium citrate" refers to $HOC(COONa)(CH_2COONa)_2.2H_2O$, and is used interchangeably with sodium citrate dihydrate, citric acid trisodium salt dihydrate, sodium citrate tribasic dihydrate and trisodium citrate dihydrate.

In some embodiments, the citrate source is citric acid, sodium citrate monobasic, sodium citrate dibasic, sodium citrate tribasic, potassium citrate monobasic, potassium citrate dibasic, potassium citrate tribasic, magnesium citrate, magnesium citrate tribasic, calcium citrate tribasic, silver citrate or silver dihydrogen citrate, or a mixture of two or more of these. In some embodiments, the citrate source is citric acid, sodium citrate monobasic, sodium citrate dibasic, sodium citrate tribasic, potassium citrate monobasic, potassium citrate dibasic, potassium citrate tribasic, magnesium citrate, magnesium citrate tribasic or calcium citrate tribasic, or a mixture of two or more of these. In some embodiments, the citrate source is citric acid, sodium citrate monobasic, sodium citrate dibasic, sodium citrate tribasic, potassium citrate monobasic, potassium citrate dibasic or potassium citrate tribasic, or a mixture of two or more of these. In some embodiments, the citrate source is citric acid, sodium citrate monobasic, sodium citrate dibasic or sodium citrate tribasic, or a mixture of two or more of these. In some embodiments, the citrate source is citric acid, sodium citrate tribasic, or a mixture thereof. In some embodiments, the citrate source is sodium citrate. In some embodiments, the citrate source is citric acid. In some embodiments, the citrate source is silver dihydrogen citrate.

Because the provided compositions are aqueous, a provided composition containing a citrate source will contain one or more citrate species in differing amounts according to various factors, such as other solvents present, other ions present, temperature, etc. Therefore, as is customary in the art, in some embodiments a provided composition containing a citrate source is described by reference to its constituent components prior to being combined, e.g., "water, propylene glycol, and sodium citrate", recognizing that sodium citrate in aqueous solution at equilibrium will exist as one or more citrate species. A weight percentage ("w/w") of such a component refers to the amount of the component as measured prior to combination. For example, a composition resulting from the combination of 79.50 g water, 20 g propylene glycol and 0.50 g sodium citrate can be described as a composition containing "water (79.50% w/w), propylene glycol (20% w/w) and sodium citrate (0.50% w/w)".

In some embodiments, a provided composition containing a citrate source is described as containing a percentage "citrate". In many such embodiments, the weight percentage "citrate" is determined without regard to the remainder of the citrate source, and considering the tribasic form of citric acid, i.e., $HOC(COO—)(CH_2COO^-)_2$. For example, sodium citrate is 64.3% w/w "citrate", because the molecular weight of $HOC(COONa)(CH_2COONa)_2.2H_2O$ is 294.1 and the molecular weight of $HOC(COO—)(CH_2COO^-)_2$ is 189.1, which is 64.3% of 294.1. Accordingly, a provided composition described as containing 0.25% w/w sodium citrate could equally be described as containing 0.16% w/w citrate. Such descriptions are especially useful when more than one source of citrate is used to make a provided composition.

For example, a provided composition described as containing 0.16% w/w citrate could be prepared in any number of various ways and/or through use of any of a variety of citrate sources. The % citrate of some exemplary citrate sources is shown below.

| citrate source | MW | % citrate |
|---|---|---|
| sodium citrate tribasic dihydrate | 294.1 | 64.3 |
| sodium citrate monobasic (anh.) | 214.1 | 88.3 |
| sodium citrate dibasic sesquihydrate | 263.1 | 71.9 |
| potassium citrate tribasic monohydrate | 324.4 | 58.3 |
| potassium citrate monobasic (anh.) | 230.2 | 82.2 |
| magnesium citrate | 214.4 | 88.2 |
| magnesium citrate tribasic nonahydrate | 613.3 | 61.7 |
| (contains 2 equivalents of citrate) | | (378.2/613.3)*100 |

From such values, one skilled in the art can easily determine appropriate weight percentages of any given citrate source(s). Weight percentages of exemplary citrate sources equivalent to 0.16% w/w citrate are shown below.

| citrate source | % w/w citrate source (measured) | % w/w citrate (calculated) |
| --- | --- | --- |
| sodium citrate tribasic dihydrate | 0.25 | 0.16 |
| sodium citrate monobasic (anh.) | 0.18 | 0.16 |
| sodium citrate dibasic sesquihydrate | 0.22 | 0.16 |
| potassium citrate tribasic monohydrate | 0.27 | 0.16 |
| potassium citrate monobasic (anh.) | 0.19 | 0.16 |
| magnesium citrate | 0.18 | 0.16 |
| magnesium citrate tribasic nonahydrate | 0.26 | 0.16 |

Those skilled in the art can readily calculate the appropriate amounts of citrate source(s) to use in a composition to obtain the desired % w/w citrate. Those skilled in the art will also recognize that solubility limits of different citrate sources will set upper limits of weight percentages achievable in a composition.

Spore-Germinating Agents: Iodide Source.

In some embodiments, provided compositions include a spore germinating agent that is or includes an iodide source. Because iodide is the conjugate base of a strong acid (HI), in aqueous solution it exists essentially as the species $I^-$ (iodide), but may also form more complex species. For the purposes of the present invention, the collective anionic species in solution attributable to an iodide source will be referred to as "iodide", recognizing both that other iodine-containing species may be present and that they are customarily not considered by those skilled in the art owing to their extremely small concentration relative to $I^-$. As used herein, an "iodide source" is any chemical species that produces or exists at least in part as iodide in aqueous solution. Examples of iodide sources include potassium iodide (KI), sodium iodide (NaI), lithium iodide (Li), cesium iodide (CsI), zinc iodide (ZnI), copper(I) iodide (CuI), calcium iodide ($CaI_1$), barium iodide ($BaI_2$), magnesium iodide ($MgI_2$), ammonium iodide ($NH_4I$), tetrabutyl ammonium iodide (($CH_3CH_2CH_2CH_2)_4NI$) and boron triiodide ($BI_3$), including anhydrous forms and hydrates (both of which are intended at every mention herein unless otherwise specified).

In some embodiments, the iodide source is potassium iodide, sodium iodide, lithium iodide, cesium iodide, zinc iodide, copper(I) iodide, calcium iodide, barium iodide, magnesium iodide, ammonium iodide, tetrabutyl ammonium iodide or boron triiodide, or a mixture of two or more of these. In some embodiments, the iodide source is potassium iodide, sodium iodide, calcium iodide, magnesium iodide, ammonium iodide or tetrabutyl ammonium iodide, or a mixture of two or more of these. In some embodiments, the iodide source is potassium iodide, sodium iodide, calcium iodide or magnesium iodide, or a mixture of two or more of these. In some embodiments, the iodide source comprises is iodide, ammonium iodide or tetrabutyl ammonium iodide, or a mixture of two or more of these. In some embodiments, the iodide source is potassium iodide.

Because the provided compositions are aqueous, a provided composition containing an iodide source will contain iodide in an amount according to various factors, such as other solvents present, other ions present, temperature, etc. Therefore, as is customary in the art, in some embodiments a provided composition containing an iodide source is described by reference to its constituent components prior to being combined, e.g., "water, propylene glycol, and potassium iodide", recognizing that potassium iodide in aqueous solution at equilibrium will exist as iodide. A weight percentage ("w/w") of such a component refers to the amount of the component as measured prior to combination. For example, a composition resulting from the combination of 79.50 g water, 20 g propylene glycol and 0.50 g potassium iodide can be described as a composition containing "water (79.50% w/w), propylene glycol (20% w/w) and potassium iodide (0.50% w/w)".

In some embodiments, a provided composition containing an iodide source is described as containing a percentage "iodide". In these embodiments, the weight percentage "iodide" is determined without regard to the remainder of the iodide source. For example, potassium iodide is 76.4% w/w "iodide", because the molecular (atomic) weight of KI is 166.0 and the molecular (atomic) weight of F is 126.9, which is 76.4% of 166.0. Accordingly, a provided composition described as containing 0.25% w/w potassium iodide could equally be described as containing 0.19% w/w iodide. Such descriptions are especially useful when more than one source of iodide is used to make a provided composition.

In a manner analogous to that described above for citrate sources, those skilled in the art can easily determine appropriate weight percentages of any given iodide source(s), and can readily calculate the appropriate amounts of iodide source(s) to use in a composition to obtain the desired % w/w iodide. Those skilled in the art will also recognize that solubility limits of different iodide sources will set upper limits of weight percentages achievable in a composition.

Solvents

A provided composition contains an organic solvent. The organic solvent can be a single organic liquid or a mixture of two or more organic liquids. Suitable organic solvents include glycols, such as ethylene glycol (1,2-ethanediol), propylene glycols (1,2-propanediol ("propylene glycol"); 1,3-propanediol), butylene glycols, (1,2-butanediol ("butylene glycol"); 1,3-butanediol; 1,4-butanediol; 2,3-butanediol), diethylene glycol (bis(2-hydroxyethyl) ether), and the like; glycerine; glycol ethers, such as ethylene glycol monomethyl ether, ethylene glycol monoethyl ether, ethylene glycol monopropyl ether, ethylene glycol monoisopropyl ether, ethylene glycol monobutyl ether, ethylene glycol monophenyl ether, ethylene glycol monobenzyl ether, diethylene glycol monomethyl ether, diethylene glycol monoethyl ether, diethylene glycol mono-n-butyl ether, ethylene glycol dimethyl ether, ethylene glycol diethyl ether, ethylene glycol dibutyl ether, and the like; polyethylene glycols, such as PEG-200 and PEG-400; and dimethyl isosorbide.

In some embodiments, the organic solvent is glycerine, a glycol, or a mixture thereof. In some embodiments, the organic solvent is glycerine. In some embodiments, the organic solvent is a glycol. In some embodiments, the organic solvent is glycerine, propylene glycol, butylene glycol, or a mixture of two or more of these. In some embodiments, the organic solvent is a mixture of glycerine and propylene glycol. In some embodiments, the organic solvent is a mixture of glycerine and butylene glycol. In some embodiments, the organic solvent is a mixture of propylene glycol and butylene glycol. In some embodiments, the organic solvent is propylene glycol. In some embodiments, the organic solvent is butylene glycol.

Additional Description of Certain Embodiments

In some embodiments, a provided composition comprises a spore-germinating agent that "consists essentially of" one or more recited components. Such language refers to a composition that can include, in addition to the specifically recited spore-germinating agent, a plurality of components that do not significantly affect the spore-germinating activity of the composition.

Sporicidal Compositions

In some embodiments {A1}: a provided sporicidal composition comprises: water; an amount $q_s$ of organic solvent, wherein $q_s$ is about 5% to about 60% w/w; and an amount $q_{g1}$ of spore-germinating agent, wherein $q_{g1}$ is about 0.05% to about 5% w/w. In some embodiments {A2}: a provided sporicidal composition is as {A1}, and the spore germinating agent comprises an amount $q_{i1}$ of iodide source, or an amount $q_{c1}$ of citrate source, or a combination thereof; wherein $q_{g1} \geq q_{i1}+q_{c1}$, and at least one of $q_{i1}$ and $q_{c1}$ is at least about 0.05% w/w. In some embodiments {A3}: a provided sporicidal composition is as {A1}, and the spore germinating agent consists essentially of an amount $q_{i1}$ of iodide source, or an amount $q_{c1}$ of citrate source, or a combination thereof; wherein $q_{g1} \geq q_{i1}+q_{c1}$, and at least one of $q_{i1}$ and $q_{c1}$ is at least about 0.05% w/w. In some embodiments {A4}: a provided sporicidal composition is as {A1}, and the spore germinating agent consists essentially of an amount $q_{i1}$ of iodide source, or an amount $q_{c1}$ of citrate source, or a combination thereof; wherein $q_{g1}=q_{i1}+q_{c1}$, and at least one of $q_{i1}$ and $q_{c1}$ is at least about 0.05% w/w. In some embodiments {A*}: a provided sporicidal composition is as any one of {A1} to {A4}.

In some embodiments, a provided sporicidal composition is as {A*}, and $q_{g1}$ is {B1}: about 0.10% to about 4.0% w/w, {B2}: about 0.10% to about 3.0% w/w, or {B3}: about 0.10% to about 2.0% w/w. In some embodiments {B4}: a provided sporicidal composition is as {A*}, $q_{g1}$ is as any of {B1} to and at least one of $q_{i1}$ and $q_{c1}$ is at least about 0.10% w/w. In some embodiments {B5}: a provided sporicidal composition is as {A*}, and $q_{g1}$ is about 0.10% to about 2.3% w/w. In some embodiments {B6}: a provided sporicidal composition is as {A*}, $q_{g1}$ is as {B5}, and at least one of $q_{i1}$ and $q_{c1}$ is at least about 0.10% w/w. In some embodiments {B*}: a provided sporicidal composition is as any one of {B1} to {B6}.

In some embodiments, a provided sporicidal composition is as {B*}, and at least one of $q_{i1}$ and $q_{c1}$ is {C1}: about 0.10% to about 1.0% w/w, {C2}: about 0.15% to about 0.90% w/w, {C3}: about 0.20% to about 0.80% w/w, {C4}: about 0.25% to about 0.75% w/w, {C5}: about 0.10% to about 0.40% w/w, {C6}: about 0.15% to about 0.35% w/w, {C7}: about 0.15% to about 0.90% w/w, {C8}: about 0.20% to about 0.30% w/w, {C9}: about 0.25% w/w, {C10}: about 0.35% to about 0.65% w/w, {C11}: about 0.40% to about 0.60% w/w, {C12}: about 0.45% to about 0.55% w/w, {C13}: about 0.50% w/w, {C14}: about 0.60% to about 0.90% w/w, {C15}: about 0.65% to about 0.85% w/w, {C16}: about 0.70% to about 0.80% w/w, {C17}: about 0.75% w/w, {C18}: about 0.85% to about 1.15% w/w, {C19}: about 0.90% to about 1.10% w/w, {C20}: about 0.95% to about 1.05% w/w, {C21}: about 1.0% w/w, or {C22}: about 0.75% to about 0.90% w/w. In some embodiments {C*}: a provided sporicidal composition is as any one of {C1} to {C22}.

In some embodiments, a provided sporicidal composition is as {C*}, and the other of $q_{i1}$ and $q_{c1}$ is {D1}: up to about 1.0%, {D2}: at least about 0.10% w/w, {D3}: about 0.10% to about 1.0% w/w, {D4}: about 0.15% to about 0.90% w/w, {D5}: about 0.20% to about 0.80% w/w, {D6}: about 0.25% to about 0.75% w/w, {D7}: about 0.10% to about 0.40% w/w, {D8}: about 0.15% to about 0.35% w/w, {D9}: about 0.15% to about 0.90% w/w, {D10}: about 0.20% to about 0.30% w/w, {D11}: about 0.25% w/w, {D12}: about 0.35% to about 0.65% w/w, {D13}: about 0.40% to about 0.60% w/w, {D14}: about 0.45% to about 0.55% w/w, {D15}: about 0.50% w/w, {D16}: about 0.60% to about 0.90% w/w, {D17}: about 0.65% to about 0.85% w/w, {D18}: about 0.70% to about 0.80% w/w, {D19}: about 0.75% w/w, {D20}: up to about 1.30% w/w, {D21}: about 0.85% to about 1.15% w/w, or {D22}: about 1.0% w/w. In some embodiments {D*}: a provided sporicidal composition is as any one of {D1} to {D22}.

In some embodiments {E1}: a provided sporicidal composition comprises: water; an amount $q_s$ of organic solvent, wherein $q_s$ is about 5% to about 60% w/w; and an amount $q_{g2}$ of spore-germinating agent, wherein $q_{g2}$ is about 0.03% to about 3.8% w/w. In some embodiments {E2}: a provided sporicidal composition is as {E1}, and the spore germinating agent comprises an amount $q_{i2}$ of iodide, or an amount $q_{c1}$ of citrate, or a combination thereof; wherein $q_{g2} \geq q_{i2}+q_{c2}$; and one or both of (a) and (b): (a) $q_{i2}$ is about 0.04% to about 3.8% w/w; (b) $q_{c2}$ is about 0.03% to about 3.2% w/w. In some embodiments {E3}: a provided sporicidal composition is as {E1}, and the spore germinating agent consists essentially of an amount $q_{i2}$ of iodide, or an amount $q_{c1}$ of citrate, or a combination thereof; wherein $q_{g2} \geq q_{i2}+q_{c2}$; and one or both of (a) and (b): (a) $q_{i2}$ is about 0.04% to about 3.8% w/w; (b) $q_{c1}$ is about 0.03% to about 3.2% w/w. In some embodiments {E4}: a provided sporicidal composition is as {E1}, and the spore germinating agent consists essentially of an amount $q_{i2}$ of iodide, or an amount $q_{c2}$ of citrate, or a combination thereof; wherein $q_{g2}=q_{i2}+q_{c2}$; and one or both of (a) and (b): (a) $q_{i2}$ is about 0.04% to about 3.8% w/w; (b) $q_{c2}$ is about 0.03% to about 3.2% w/w. In some embodiments {E*}: a provided sporicidal composition is as any one of {E1} to {E4}.

In some embodiments, a provided sporicidal composition is as {E*}, and $q_{g2}$ is {F1}: about 0.06% to about 3.1% w/w, {F2}: about 0.06% to about 2.3% w/w, or {F3}: about 0.06% to about 1.5% w/w. In some embodiments {F4}: a provided sporicidal composition is as {E*}, $q_{g2}$ is as any of {F1} to {F3}, and one or both of (a) and (b): (a) $q_{i2}$ is at least about 0.08% w/w; (b) $q_{c2}$ is at least about 0.06% w/w. In some embodiments {F*}: a provided sporicidal composition is as any one of {F1} to {F4}.

In some embodiments, a provided sporicidal composition is as {F*}, and one or both of (a) and (b), wherein {G1}: (a) $q_{i2}$ is about 0.08% to about 0.76% w/w; (b) $q_{c2}$ is about 0.06% to about 0.64% w/w; {G2}: (a) $q_{i2}$ is about 0.11% to about 0.69% w/w; (b) $q_{c2}$ is about 0.10% to about 0.58% w/w; {G3}: (a) $q_{i2}$ is about 0.15% to about 0.61% w/w; (b) $q_{c2}$ is about 0.13% to about 0.51% w/w; {G4}: (a) $q_{i2}$ is about 0.19% to about 0.57% w/w; (b) $q_{c2}$ is about 0.16% to about 0.48% w/w; {G5}: (a) $q_{i2}$ is about 0.08% to about 0.31% w/w; (b) $q_{c2}$ is about 0.06% to about 0.26% w/w; {G6}: (a) $q_{i2}$ is about 0.11% to about 0.27% w/w; (b) $q_{c2}$ is about 0.10% to about 0.23% w/w; {G7}: (a) $q_{i2}$ is about 0.13% to about 0.23% w/w; (b) $q_{c2}$ is about 0.13% to about 0.19% w/w; {G8}: (a) $q_{i2}$ is about 0.19% w/w; (b) $q_{c2}$ is about 0.16% w/w; {G9}: (a) $q_{i2}$ is about 0.27% to about 0.50% w/w; (b) $q_{c2}$ is about 0.23% to about 0.42% w/w; {G10}: (a) $q_{i2}$ is about 0.31% to about 0.46% w/w; (b) $q_{c2}$ is about 0.26% to about 0.39% w/w; {G11}: (a) $q_{i2}$ is about 0.34% to about 0.42% w/w; (b) $q_{c2}$ is about 0.29% to about 0.35% w/w; {G12}: (a) $q_{i2}$ is about 0.38% w/w; (b) $q_{c2}$ is about 0.32% w/w; {G13}: (a) $q_{i2}$ is about 0.46% to about 0.69% w/w; (b) $q_{c2}$ is about 0.39% to about 0.61% w/w; {G14}: (a) $q_{i2}$ is about 0.50% to about 0.65% w/w; (b) $q_{c2}$ is about 0.42% to about 0.55% w/w; {G15}: (a) $q_{i2}$ is about 0.53% to about 0.61% w/w; (b) $q_{c2}$ is about 0.45% to about 0.51% w/w; {G16}: (a) $q_{i2}$ is about 0.57% w/w; (b) $q_{c2}$ is about 0.48% w/w; {G17}: (a) $q_{i2}$ is about 0.65% to about 0.88% w/w; (b) $q_{c2}$ is about 0.55% to about 0.74% w/w;

{G18}: (a) $q_{i2}$ is about 0.69% to about 0.84% w/w; (b) $q_{c2}$ is about 0.58% to about 0.71% w/w; {G19}: (a) $q_{i2}$ is about 0.73% to about 0.80% w/w; (b) $q_{c2}$ is about 0.61% to about 0.68% w/w; {G20}: (a) $q_{i2}$ is about 0.76% w/w; (b) $q_{c2}$ is about 0.64% w/w; {G21}: (a) $q_{i2}$ is about 0.65% to about 0.88% w/w; (b) $q_{c2}$ is about 0.73 to about 0.91% w/w; {G22}: (a) $q_{i2}$ is about 0.69% to about 0.84% w/w; (b) $q_{c2}$ is about 0.76% to about 0.88% w/w; {G23}: (a) $q_{i2}$ is about 0.73% to about 0.80% w/w; (b) $q_{c2}$ is about 0.79% to about 0.85% w/w; {G24}: (a) $q_{i2}$ is about 0.76% w/w; (b) $q_{c2}$ is about 0.82% w/w. In some embodiments {G*}: a provided sporicidal composition is as any one of {G1} to {G24}.

In some embodiments, a provided sporicidal composition is as any one of {A*}, {B*}, {C*}, {D*}, {E*}, {F*} or {G*}, and $q_s$ is {H1}: about 5% to about 50% w/w, {H2}: about 10% to about 50% w/w, {H3}: about 5% to about 40% w/w, {H4}: about 10% to about 40% w/w, {H5}: about 5% to about 30% w/w, {H6}: about 10% to about 30% w/w, {H7}: about 10% to about 25% w/w, or {H8}: about 15% to about 25% w/w. In some embodiments {H*}: a provided sporicidal composition is as any one of {H1} to {H7}.

In some embodiments, {I1}: a provided sporicidal composition is as any one of {A*}, {B*}, {C*}, {D*}, {E*}, {F*}, {G*} or {H*}, and the organic solvent comprises glycerine, propylene glycol or butylene glycol. In some embodiments, {I2}: a provided sporicidal composition is as any one of {A*}, {B*}, {C*}, {D*}, {E*}, {F*}, {G*} or {H*}, and the organic solvent consists essentially of glycerine, propylene glycol, butylene glycol, or a mixture of two or more of these. In some embodiments, {I3}: a provided sporicidal composition is as any one of {A*}, {B*}, {C*}, {D*}, {E*}, {F*}, {G*} or {H*}, and the organic solvent consists of glycerine, propylene glycol, butylene glycol, or a mixture of two or more of these. In some embodiments {I*}: a provided sporicidal composition is as any one of {I1} to {I3}.

In some embodiments, {J1}: a provided sporicidal composition is as any one of {A*}, {B*}, {C*}, {D*}, {E*}, {F*}, {G*}, {H*} or {I*}, and the spore-germinating agent consists essentially of an iodide source or a combination of an iodide source and a citrate source. In some embodiments, {J2}: a provided sporicidal composition is as {J1}, and the spore-germinating agent consists essentially of an iodide source. In some embodiments, {J3}: a provided sporicidal composition is as {J1} or {J2}, and the iodide source comprises potassium iodide. In some embodiments, {J4}: a provided sporicidal composition is as {J1} or {J2}, and the iodide source consists essentially of potassium iodide. In some embodiments {J*}: a provided sporicidal composition is as any one of {J1} to {J4}.

In some embodiments, {K1}: a provided sporicidal composition is as any one of {A*}, {B*}, {C*}, {D*}, {E*}, {F*}, {G*}, {H*} or {I*}, and the spore-germinating agent consists essentially of a citrate source or a combination of a citrate source and an iodide source. In some embodiments, {K2}: a provided sporicidal composition is as {K1}, and the spore-germinating agent consists essentially of a citrate source. In some embodiments, {K3}: a provided sporicidal composition is as {K1} or {K2}, and the citrate source comprises citric acid, sodium citrate monobasic or a hydrate thereof, sodium citrate dibasic or a hydrate thereof, or sodium citrate tribasic or a hydrate thereof. In some embodiments, {K4}: a provided sporicidal composition is as {K1} or {K2}, and the citrate source comprises sodium citrate tribasic dihydrate. In some embodiments, {K5}: a provided sporicidal composition is as {K1} or {K2}, and the citrate source consists essentially of one or more of citric acid, sodium citrate monobasic or a hydrate thereof, sodium citrate dibasic or a hydrate thereof, or sodium citrate tribasic or a hydrate thereof. In some embodiments, {K6}: a provided sporicidal composition is as {K1} or {K2}, and the citrate source consists essentially of one or more of sodium citrate tribasic dihydrate and citric acid. In some embodiments, {K7}: a provided sporicidal composition is as {K1} or {K2}, and the citrate source consists essentially of one or more of sodium citrate tribasic dihydrate. In some embodiments {K*}: a provided sporicidal composition is as any one of {K1} to {K7}.

Disinfecting Compositions

In some embodiments, the invention provides a disinfecting composition, comprising a provided sporicidal composition, and a disinfectant, wherein the provided sporicidal composition is as any one of {A*}, {B*}, {C*}, {D*}, {E*}, {F*}, {G*}, {H*}, {I*}, {J*} or {K*}. In some embodiments, the disinfectant comprises an alcohol disinfectant, an aldehyde disinfectant, an oxidizing disinfectant, a phenolic disinfectant, a quaternary ammonium disinfectant, chlorhexidine gluconate, polyhexamethylene biguanide (polyhexanide; PHMB) or 4-chloro-3,5-dimethylphenol (chloroxylenol; p-chloro-m-xylenol; PCMX).

In some embodiments, the disinfectant comprises an alcohol disinfectant. In some embodiments, the alcohol disinfectant comprises ethanol or isopropanol.

In some embodiments, the disinfectant comprises an aldehyde disinfectant. In some embodiments, the aldehyde disinfectant comprises formaldehyde, glutaraldehyde or o-phthalaldehyde.

In some embodiments, the disinfectant comprises an oxidizing disinfectant. In some embodiments, the oxidizing disinfectant comprises sodium hypochlorite, calcium hypochlorite, chloramine, chloramine-T, chlorine dioxide, sodium chlorite, sodium chlorate, potassium chlorate, hydrogen peroxide, iodine, peracetic acid, performic acid, potassium permanganate or potassium peroxymonosulfate.

In some embodiments, the disinfectant comprises a phenolic disinfectant. In some embodiments, the phenolic disinfectant comprises phenol, o-phenylphenol, chloroxylenol, hexachlorophene, thymol, amylmetacresol, 2,4-dichlorobenzyl alcohol or phenoxyethanol (Rose ether).

In some embodiments, the disinfectant comprises a quaternary ammonium disinfectant. In some embodiments, the quaternary ammonium disinfectant comprises benzalkonium chloride, benzethonium chloride, methylbenzethonium chloride, cetalkonium chloride, cetylpyridinium chloride, cetrimonium, cetrimide, dofanium chloride, tetraethylammonium bromide, didecyldimethylammonium chloride or domiphen bromide.

In some embodiments, the disinfectant comprises chlorhexidine gluconate. In some embodiments, the disinfectant comprises polyhexamethylene biguanide. In some embodiments, the disinfectant comprises 4-chloro-3,5-dimethylphenol.

Antiseptic Compositions

In some embodiments, the invention provides an antiseptic composition, comprising a provided sporicidal composition, and an antiseptic, wherein the provided sporicidal composition is as any one of {A*}, {B*}, {C*}, {D*}, {E*}, {F*}, {G*}, {H*}, {I*}, {J*} or {K*}. In some embodiments, the antiseptic comprises an alcohol antiseptic, a quaternary ammonium antiseptic, chlorhexidine gluconate, hydrogen peroxide, polyhexamethylene biguanide (polyhexanide; PHMB), 4-chloro-3,5-dimethylphenol (chloroxylenol; p-chloro-m-xylenol; PCMX), iodine, octenidine dihydrochloride, sodium hypochlorite, calcium hypochlorite or sodium bicarbonate.

In some embodiments, the antiseptic comprises an alcohol antiseptic. In some embodiments, the antiseptic comprises chlorhexidine gluconate. In some embodiments, the antiseptic comprises hydrogen peroxide. In some embodiments, the antiseptic comprises polyhexamethylene biguanide. In some embodiments, the antiseptic comprises 4-chloro-3,5-dimethylphenol.

In some embodiments, the antiseptic comprises iodine. In some embodiments, the iodine is at least in part in the form of an iodophor. In some embodiments, the iodophor comprises povidone-iodine ("PVP-I"). Povidone-iodine is a complex of polyvinylpyrrolidone ("PVP") and elemental iodine. See, e.g., International Specialty Products, *PVP-Iodine: Povidone Iodine Antiseptic Agent* (2004).

In some embodiments, a provided composition comprises about 8% to about 12% w/w PVP-I. In some embodiments, a provided composition comprises about 9% to about 11% w/w PVP-I. In some embodiments, a provided composition comprises about 9.5% to about 10.5% w/w PVP-I. In some embodiments, a provided composition comprises about 9.8% to about 10.2% w/w PVP-I. In some embodiments, a provided composition comprises about 10% w/w PVP-I.

In some embodiments, a provided composition comprises about 10% to about 12.5% w/w PVP-I. In some embodiments, a provided composition comprises about 10% to about 12% w/w PVP-I. In some embodiments, a provided composition comprises about 10% to about 11.5% w/w PVP-I. In some embodiments, a provided composition comprises about 10% to about 11% w/w PVP-I. In some embodiments, a provided composition comprises about 10% to about 10.5% w/w PVP-I.

In some embodiments, a provided composition comprises about 5% to about 12% w/w PVP-I. In some embodiments, a provided composition comprises about 5% to about 11% w/w PVP-I. In some embodiments, a provided composition comprises about 5% to about 10.5% w/w PVP-I. In some embodiments, a provided composition comprises about 6% to about 10.5% w/w PVP-I. In some embodiments, a provided composition comprises about 7% to about 10.5% w/w PVP-I. In some embodiments, a provided composition comprises about 8% to about 10.5% w/w PVP-I. In some embodiments, a provided composition comprises about 9% to about 10.5% w/w PVP-I.

In some embodiments, an antiseptic composition is suitable for topical administration. In some embodiments, a topical antiseptic composition is a composition according to Example 2.3, 2.4 or 2.5. Examples of products suitable for the components of these compositions are shown in the table below.

| | |
|---|---|
| hydroxyethylcellulose | Natrosol ® CS, Natrosol ® 250 HHR, Natrosol ® 250 HR, Natrosol ® 250 HX, Natrosol ® 250 M, Natrosol ® 250 MR, |
| sclerotium gum | Amigel ® , Vegetensor ® , Actigum ™ CS 6 |
| benzalkonium chloride | benzalkonium chloride (e.g., Spectrum Chemical, TCI America), Stepanquat ® 50 NF, Stepanquat ® 65 NF, Swanol ™ CA-101 |
| stearic acid[1] | stearic acid (e.g., Jeen International Corp. (Stearic Acid NF), Protameen Chemicals, Parchem; grades with lower iodine number preferred), Bergazid ™ C1835, Bergazid ™ C1852, Bergazid ™, C1892, Bergazid ™ C1895, Emersol ® 7036 NF, Pristerine ™ 4900, Pristerine ™ 4911, Pristerine ™ 9559 |
| cetyl alcohol[2] | cetyl alcohol (e.g., Jeen International Corp. (Cetyl Alcohol NF), Protameen Chemicals; grades with lower iodine number preferred), Crodacol ™ C-70, Crodacol ™ C90, Crodacol ™ C90 EP, Crodacol ™ C95, Kalcol ™ 6098, Lanette ® 16, Lipocol ® C, Tego ® Alkanol 16 |
| polyquaternium-7[3] | Cetarol ™ PQ7, Conditioneze ® 7, Dehyquart ® 701/NA, Dehyquart ® CC7 BZ, Mackernium ™ 007, Mackernium ™ 007S, Merquat ® 550, Merquat ® S, Mirapol ® 550, Salcare ® Super 7, Thorcoquat ™ 550, Zetesoft ™ PQ7 |
| distearyldimonium chloride[4] | Genamin ® DSAC, Genamin ® DSAC 75, Genamin ® DSAP, Nikkol ™ CA-3475, Protaquat ® 2HT-75, Swanol ™ CA-3475, Varisoft ® TA 100 |
| glycerol monolaurate[5] | glycerol monolaurate (e.g., Jeen International Corp., Mosselman Oleochemicals), Lauricidin ® |
| PEG-20 methyl glucose sesquistearate[6] | Glucamate ™ SSE-20, Glukosa ™ SSE-20 |
| Emulsifying Wax[7] | Emulsifying Wax NF, Polawax ™ NF |
| PEG-7 glyceryl cocoate[8] | Acconon ® CO-7, Cetarol ™ HE 7, Cetiol ® HE, Cremophor ® GC-7, Glycerox ™ HE, Hetoxide ™ GC-7, Jeechem ™ GC-7, Liponate ® GMC-7, Protachem ™ GC-7, Saboderm ™ HE, Sympatems ™ GMC 070 |
| ammonium nonoxynol-4 sulfate[9] | Alipal ™ CO 436, Rhodapex ® CO-436 |
| octoxynol 9[10] | Igepal ® CA-9, Protachem ™ OP-9, Triton ™ X-100 |
| nonoxynol-9[11] | Jeechem ™ NP-9, Protachem ™ NP-9, Tergitol ™ NP-9 |
| 4-hydroxyacetophenone | 4-hydroxyacetophenone (e.g., Sigma-Aldrich, Spectrum Chemical), Sym Save ® H |

[1] n-octadecanoic acid
[2] hexadecan-1-ol
[3] copolymer of acrylamide and diallyldimethylammonium chloride
[4] dimethyldioctadecylammonium chloride
[5] 2,3-dihydroxypropyl dodecanoate
[6] poly(oxy-1,2-ethanediyl), α-hydro-ω-hydroxy-, ether with methyl β-d-glucopyranoside (4:1), octadecanoate (2:3) (20 mol EO average molar ratio)
[7] cetearyl alcohol, PEG-150 stearate, polysorbate 60, steareth-20
[8] poly(oxy-1,2-ethanediyl), α,α',α"-1,2,3-propanetriyltris-ω-hydroxy-, monococonut acid ester (7 mol EO average molar ratio)
[9] poly(oxy-1,2-ethanediyl), α-sulfo-ω-(nonylphenoxy)-, ammonium salt
[10] poly(oxy-1,2-ethanediyl), α-[4-(1,1,3,3-tetramethylbutyl)phenyl]-ω-hydroxy-(9 mol EO average molar ratio)
[11] 2-[2-[2-[2-[2-[2-[2-[2-(4-nonylphenoxy)ethoxy]ethoxy]ethoxy]ethoxy]-ethoxy]ethoxy]ethoxy]ethanol

EXAMPLES

Example 1

Preparation of Sporicidal Compositions

Example 1.1

Topical Antiseptic Compositions Containing PVP-I

Topical antiseptic compositions containing PVP-I can be prepared according to the following general procedure.

Phase I.
1. Add DI Water (deionized water) to suitably sized vessel with propeller agitation.
2. Slowly sprinkle hydroxyethylcellulose into room temperature water with propeller agitation.
3. After addition complete, let Phase mix until hydroxyethylcellulose is dissolved.
4. If sclerotium gum is also present in formula, slowly sprinkle sclerotium gum into room temperature water with propeller agitation. After addition complete, let Phase mix until sclerotium gum is dissolved.
5. Once sclerotium gum is dissolved, begin heating batch to 83°-86° C.
6. Once temperature is reached, make sure a viscous, clear gel is formed. Product should be lump-free and uniform before adding next phase.
7. Add benzalkonium chloride. Mix until uniform.
8. Add stearic acid. Mix until uniform and melted. Let this phase mix for an additional 5-10 minutes.

Phase II.
1. Add cetyl alcohol. Mix until uniform and melted.
2. Add polyquaternium-7. Mix until uniform.
3. Add distearyldimonium chloride slowly to batch. Mix well until batch is uniform and no lumps are present.
4. Once batch is lump free, add triethanolamine to batch. After addition, mix batch for 15 minutes.
5. Make sure batch temperature remains at 83°-86° C. before continuing to next phase.

Phase III.
1. Maintain constant temperature of the batch at 83°-86° C. during the following additions.
2. Add glycerol monolaurate to the batch. Mix until melted and uniform with propeller mixing.
3. Add PEG-20 methyl glucose sesquistearate to the batch. Mix until dispersed and uniform with propeller mixing.
4. Add Emulsifying Wax NF to the batch. Mix until melted and uniform with propeller mixing. Mix batch for additional 5 minutes after addition is complete.

Phase IV.
1. Begin cooling the batch to 65° C.
2. At 65° C., add PEG-7 glyceryl cocoate to batch with propeller mixing. Mix until uniform.

Phase V.
1. Cool batch to 60° C.
2. At 60° C., add disodium ethylenediamine tetraacetate to batch. Mix until completely uniform with propeller mixing. If hydroxyacetophenone is present in the composition, pre-mix with 3% glycerine, add to batch and mix until completely uniform with propeller mixing. Make sure batch is lump free.
3. Begin slowly cooling batch to 45° C.

Phase VI. The spore-germinating agent can vary. In some formulations, it is potassium iodide, sodium citrate, citric acid, a combination of two of these, or a mixture of all three.

1. At 45° C., add the spore-germinating agent to the batch. Mix until uniform and make sure no lumps are present.
2. If an additional spore-germinating agent is present in the composition, add it to the batch. Mix until uniform and make sure no lumps are present. Repeat this step for each additional spore-germinating agent, if any, present in the composition.

Phase VII.
1. Begin cooling batch to 40° C.
2. In a separate vessel, add the following ingredients one at a time with propeller mixing: glycerine (if present in the composition), ammonium nonoxynol-4 sulfate, octoxynol-9 and nonoxynol-9
3. Once the above ingredients are uniform, slowly sprinkle povidone-iodine (PVP-I) into premixed liquids, using propeller type mixing. Mix until uniform and no lumps are present.
4. Once this premixed phase is uniform and lump free, add entire Pre Mix into Batch in Main Kettle and mix until uniform with propeller type mixing. Make sure batch is completely uniform.
5. Once batch is completely uniform, change to a sweep blade and continue to mix and cool until batch is at room temperature (25° C.).

Example 1.2

Topical PVP-I Placebo Compositions

Placebo compositions PP.A1.L3 and PP.A2.L3 were prepared according to the general procedure described in Example 1.1, but with the following differences.
1. In Phase I, polyquaternium-10 is added and mixed following addition of DI water and before addition of hydroxyethylcellulose.
2. Phase IV was conducted at 70° C. rather than 65° C.
3. Phase VI was conducted at 50° C. rather than 45° C.
4. Phase VII was conducted at 50° C. rather than 40° C.

Example 2

Constitution of Sporicidal Compositions

Example 2.1

Sporicidal Compositions Lacking Antiseptic

The indicated sporicidal compositions were composed as shown in the following table.

| identifier | solvent | (% w/w) | sodium citrate (% w/w) | potassium iodide (% w/w) |
|---|---|---|---|---|
| A1.L1 | DI H$_2$O | 79.75 | 0.25 | — |
|  | propylene glycol | 20 |  |  |
| A1.L2 | DI H$_2$O | 79.50 | 0.50 | — |
|  | propylene glycol | 20 |  |  |
| A1.L3 | DI H$_2$O | 79.25 | 0.75 | — |
|  | propylene glycol | 20 |  |  |
| A2.L1 | DI H$_2$O | 79.75 | — | 0.25 |
|  | propylene glycol | 20 |  |  |
| A2.L2 | DI H$_2$O | 79.50 | — | 0.50 |
|  | propylene glycol | 20 |  |  |
| A2.L3 | DI H$_2$O | 79.25 | — | 0.75 |
|  | propylene glycol | 20 |  |  |

Example 2.2

Topical PVP-I Placebo Compositions

PVP-I placebo compositions were composed as shown in the following table (numbers are expressed in percentage w/w).

| Component | PP.A1.L3 | PP.A2.L3 |
|---|---|---|
| deinonized water | 45.10 | 45.10 |
| sodium citrate | 0.75 | 0.00 |
| potassium iodide | 0.00 | 0.75 |
| propylene glycol | 15.00 | 15.00 |
| polyquaternium-10 | 39.15 | 39.15 |
| hydroxyethylcellulose | (total) | (total) |
| benzalkonium chloride (50% solution) | | |
| stearic acid | | |
| cetyl alcohol | | |
| distearyldimonium chloride | | |
| triethanolamine | | |
| glycerol monolaurate | | |
| PEG-20 methyl glucose sesquistearate | | |
| Emulsifying Wax | | |
| caprylic/capric triglycerides | | |
| ethylenediamine tetraacetate | | |
| ammonium nonoxynol-4 sulfate | | |
| octoxynol-9 | | |
| nonoxynol-9 | | |

Example 2.3

Topical Antiseptic Compositions Containing Propylene Glycol

These compositions can be prepared according to the procedure of Example 1.2, and were composed as shown in the following table (numbers are expressed in percentage w/w).

| Component | FF-10.1 | FF-10.2 | FF-10.3 |
|---|---|---|---|
| deinonized water | 35.10 | 35.10 | 35.10 |
| sodium citrate | 0.75 | 0.00 | 0.75 |
| potassium iodide | 0.00 | 0.75 | 0.75 |
| propylene glycol | 15.00 | 15.00 | 15.00 |
| povidone-iodine | 10.00 | 10.00 | 10.00 |
| polyquaternium-10 | 39.15 | 39.15 | 38.40 |
| hydroxyethylcellulose | (total) | (total) | (total) |
| benzalkonium chloride (50% solution) | | | |
| stearic acid | | | |
| cetyl alcohol | | | |
| distearyldimonium chloride | | | |
| triethanolamine | | | |
| glycerol monolaurate | | | |
| PEG-20 methyl glucose sesquistearate | | | |
| Emulsifying Wax | | | |
| caprylic/capric triglycerides | | | |
| ethylenedia mine tetraacetate | | | |
| ammonium nonoxynol-4 sulfate | | | |
| octoxynol-9 | | | |
| nonoxynol-9 | | | |

Example 2.4

Topical Antiseptic Compositions Containing Butylene Glycol

The formulations were prepared according to the procedure of Example 1.1, and were composed as shown in the following table (numbers are expressed in percentage w/w).

| Component | FF-B.1 | FF-B.2 |
|---|---|---|
| deinonized water | 27.95 | 27.95 |
| potassium iodide | 0.75 | 0.50 |
| citric acid | 0.25 | 0.25 |
| glycerine | 0.00 | 5.00 |
| butylene glycol | 20.00 | 15.00 |
| povidone-iodine | 10.00 | 10.00 |
| sclerotium gum | 41.05 | 41.30 |
| benzalkonium chloride (50% solution) | (total) | (total) |
| stearic acid | | |
| cetyl alcohol | | |
| polyquaternium-7 | | |
| distearyldimonium chloride | | |
| triethanolamine | | |
| glycerol monolaurate | | |
| PEG-20 methyl glucose sesquistearate | | |
| Emulsifying Wax | | |
| PEG-7 glyceryl cocoate | | |
| ethylenedia mine tetraacetate | | |
| ammonium nonoxynol-4 sulfate | | |
| octoxynol-9 | | |
| nonoxynol-9 | | |

Example 2.5

Topical Antiseptic Compositions Containing Glycerine

The compositions were prepared according to the procedure of Example 1.1, but with the following differences: Phase IV was conducted at 70° C., and Phase VI was conducted at 50° C. They were composed as shown in the following table (numbers are expressed in percentage w/w).

| Component | FF-G.1 | FF-G.2 |
|---|---|---|
| deinonized water | 36.20 | 35.20 |
| potassium iodide | 1.00 | 1.00 |
| citric acid | 0.50 | 0.50 |
| sodium citrate | 0.50 | 0.50 |
| glycerine | 10.00 | 10.00 |
| povidone-iodine | 10.00 | 10.00 |
| hydroxyethylcellulose | 41.80 | 42.80 |
| benzalkonium chloride (50% solution) | (total) | (total) |
| stearic acid | | |
| cetyl alcohol | | |
| polyquaternium-7 | | |
| distearyldimonium chloride | | |
| triethanolamine | | |
| glycerol monolaurate | | |
| PEG-20 methyl glucose sesquistearate | | |
| Emulsifying Wax | | |
| PEG-7 glyceryl cocoate | | |
| ethylenedia mine tetraacetate | | |
| ammonium nonoxynol-4 sulfate | | |
| octoxynol-9 | | |
| nonoxynol-9 | | |
| hydroxyacetophenone | | |

Example 3

Activity of Sporicidal Compositions

Example 3.1

Sporicidal Compositions Lacking Antiseptic

Test Samples.

Compositions according to Examples 2.1 (sporicidal compositions lacking antiseptic) and 2.2 (topical PVP-I placebo compositions) were prepared.

Test Parameters.

| microorganism: | C. difficile ATCC 43598 (endospores) | exposure temp: | room temp. |
| --- | --- | --- | --- |
| subculture no.: | n/a | type of sample: | solvent in dilution |
| growth medium: | C. difficile agar | neutralize used: | Dey/Engley (D/E) broth, 20 mL |
| culture dilution medium: | phosphate-buffered saline (PBS) | no. of replicates: | Duplicate |
| inoculum volume: | 0.01 mL | plate incubation: | 36.0 ± 1° C. (anaerobic conditions) |
| contact times: | 30 minutes | incubation time: | ~72 hours |
| elapsed heat shock: | ~8 minutes | heat shock temp.: | 70 ± 2° C. |

Test Procedure.

A 0.990 mL volume of each test sample (for PP, 1.00±0.01 g weighed and tested) was inoculated with 0.01 mL of a *C. difficile* endospore suspension, vortex mixed, and the vessel was allowed to react for 30 minutes. After the 30-minute contact time, the inoculated test substances were subjected to ~70° C. for 8 minutes. Each substance was then neutralized with 20 mL Dey/Engley (D/E) broth, and enumerated using spread plate techniques.

Results.

Spore count reductions are shown below and in FIG. 1.

| sample | replicate | CFU/mL (×10$^5$) | Reduction from Control, 8 min. (%)[1] |
| --- | --- | --- | --- |
| time = 0 | 1 | 15.00 | — |
|  | 2 | 15.50 |  |
| Control[2] | 1 | 15.50 | — |
|  | 2 | 17.00 |  |
| A1.L1 | 1 | 1.63 | 89.5 |
|  | 2 | 1.83 | 89.2 |
| A1.L2 | 1 | 1.39 | 91.0 |
|  | 2 | 1.39 | 91.8 |
| A1.L3 | 1 | 1.39 | 91.0 |
|  | 2 | 1.57 | 90.8 |
| A2.L1 | 1 | 1.79 | 88.5 |
|  | 2 | 1.36 | 92.0 |
| A2.L2 | 1 | 1.53 | 90.1 |
|  | 2 | 1.18 | 93.1 |
| A2.L3 | 1 | 1.55 | 90.0 |
|  | 2 | 1.90 | 88.8 |
| PP.A1.L3 | 1 | 3.38 | 78.2 |
|  | 2 | 2.96 | 82.6 |
| PP.A2.L3 | 1 | 2.63 | 83.9 |
|  | 2 | 2.92 | 82.8 |

[1]% Reduction = 100 × (B − A)/B
A = number of surviving bacteria (spores) in sample after the contact time
B = number of bacteria (spores) in the untreated sample immediately after inoculation and/or the contact time
[2]Saline Example 3.2

Topical Antiseptic Compositions Containing Butylene Glycol and/or Glycerine

Test Parameters.

Microorganism: *Clostridium difficile* ATCC 43603 (spores)

Time Intervals: 0-Time (numbers control) 1 min, 2 min, 3 min, 5 min, 10 min

Media and Equipment: Neutralization Broth (Letheen Broth with 0.05% Na$_2$S$_2$O$_3$)

Anaerobic Agar ("AA")

Saline, 0.85%

36° C.±1° C. Incubator

Calibrate Timer

Miscellaneous

Balance

Test Procedure.

Preparation of the Spore Suspension.

*Clostridium difficile* was grown with AA anaerobically at 36° C.-38° C. for 20 days. Spores were aseptically harvested with sterile 80% Isopropyl Alcohol ("IPA") and collected in a sterile vessel. The spore suspension was then centrifuged for 20 minutes at 5000 rpm and the pellets re-suspended in sterile 80% IPA to achieve a final concentration between 1.0×10$^7$ and 5.0×10$^7$ viable spores/mL. Plate counting was performed to verify that spores count is appropriate.

Inoculation of the Test Material and Enumeration of the Organism.

1 gram aliquot of the test material was transferred to a sterile glass jar. 104 aliquots of the prepared test organism were inoculated into the test material to achieve a concentration between 1.0×10$^5$ and 5.0×10$^5$ spores/mL. The jar was mixed immediately. After the appropriate contact time, 99 mL of the neutralization broth was added into each jar and thoroughly mixed. Recovery was performed by plate count as follows:

10 mL (to give a dilution of 10$^{-1}$ plated with AA.

1 mL (to give a dilution of 10$^{-2}$ plated with AA.

1 mL to 9.0 mL of saline followed by ten-fold serial dilution to achieve 10$^{-3}$ to 10$^{-5}$ dilutions and plating 1.0 mL aliquots onto AA.

The plates were then incubated anaerobically at 36° C.±1° C. for 4 to 5 days. At the end of the incubation periods, the plates were counted using a Quebec colony counter and the number of viable organisms was determined.

Numbers Control.

1.0 mL aliquot of sterile saline was transferred to a sterile glass jar. 104 aliquots of the prepared test organism were inoculated into the test material to achieve a concentration between 1.0×10$^5$ and 5.0×10$^5$ spores/mL. The jar was mixed immediately. After the appropriate contact time, 99 mL of the neutralization broth was added into each jar and thoroughly mixed. Ten-fold serial dilutions were made thereafter into 9.0 mL of neutralization broth. 2×1.0 mL from each dilution tube was plated into sterile Petri dishes and poured, plated, incubated and counted as above.

Log Reduction and % Reduction Calculation.

$$\log_{10} \text{reduction} = \log_{10} \text{initial bacterial population (Numbers Control)} - \log_{10} \text{number of survivors}$$

$$\% \text{ reduction} = \frac{\text{initial bacterial population (Numbers Control)} - \text{number survivors (Test Sample)}}{\text{initial bacterial population (Numbers Control)}} \times 100$$

Results.

Figure 2:
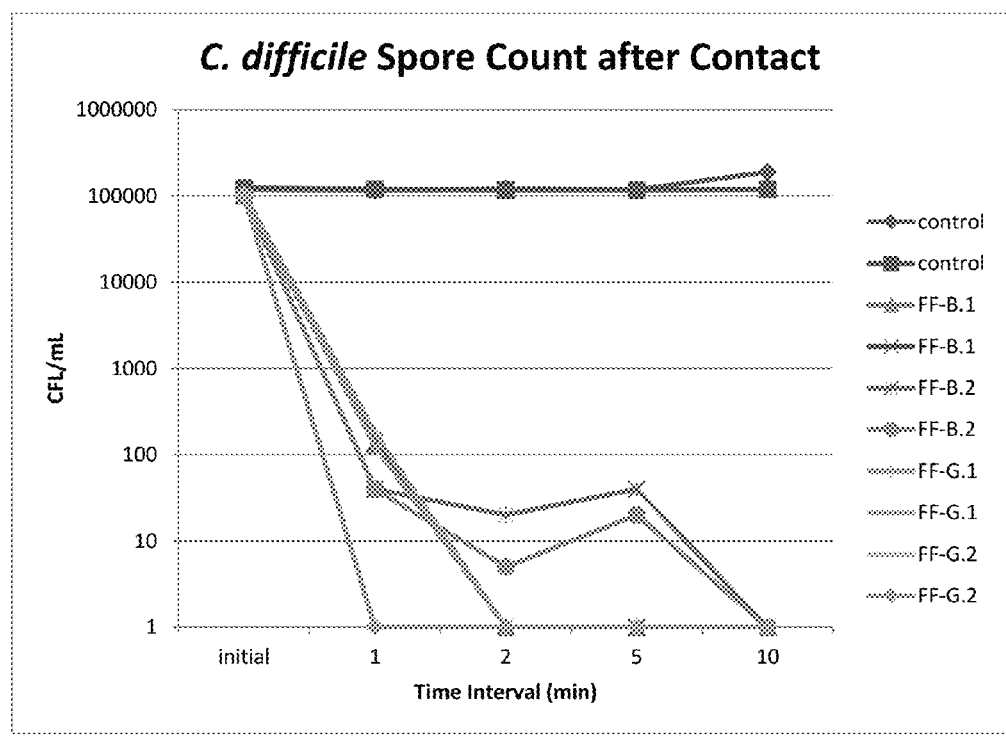
FIG. 2 shows reduction in *C. difficile* spore count after contact with provided compositions according to Example 3.2.

Spore count reductions are shown below and in FIG. 2.

| Sample | initial count CFU/mL × $10^3$ | 1 min CFU/mL × $10^3$ | 2 min CFU/mL × $10^3$ | 5 min CFU/mL × $10^3$ | 10 min CFU/mL × $10^3$ |
|---|---|---|---|---|---|
| Control | 120. | 115 | 121 | 118 | 190 |
|  | 124 | 120. | 117 | 117 | 120 |
| log reduction: |  | 0.0163 | 0.0108 | 0.0163 | −0.104 |
| % reduction: |  | 3.69 | 2.46 | 3.69 | −27.1 |
| FF-B.1 | 100. | 0.130 | 0 | 0 | 0 |
|  | 104 | 0.140 | 0 | 0 | 0 |
| log reduction: |  | 2.88 | N/A | N/A | N/A |
| % reduction: |  | 99.9 | 100. | 100. | 100. |
| FF-B.2 | 100. | 0.0400 | 0.0200 | 0.0400 | 0 |
|  | 100. | 0.0400 | 0.0050 | 0.0200 | 0 |
| log reduction: |  | 3.66 | 3.90 | 3.52 | N/A |
| % reduction: |  | 99.9 | 99.9 | 99.9 | 100. |
| FF-G.1 | 106 | 0.180 | 0 | 0 | 0 |
|  | 108 | 0.125 | 0 | 0 | 0 |
| log reduction: |  | 2.85 | N/A | N/A | N/A |
| % reduction: |  | 99.9 | 100. | 100. | 100. |
| FF-G.2 | 100. | 0 | 0 | 0 | 0 |
|  | 100. | 0 | 0 | 0 | 0 |
| log reduction: |  | N/A | N/A | N/A | N/A |
| % reduction: |  | 100. | 100. | 100. | 100. |

Example 3.3

Topical Antiseptic Compositions on Hands

Test Composition.

Compositions according to Example 2.5 (topical antiseptic compositions containing glycerine).

Experimental Samples.

| Sample | Test composition? | Test condition |
|---|---|---|
| 1 (control) | No | Spore contamination, and no intervention. |
| 2 (rinse) | No | Spore contamination followed by a 30 s rinse |
| 3 (wash) | No | Spore contamination followed by a 15 s hand wash with a bactericidal soap and a 15 s rinse |
| 4 | Yes | Spore contamination followed by application of test composition |
| 5 | Yes | Application of test composition followed by spore contamination |
| 6 | Yes | Application of test composition followed by spore application followed by reapplication of test composition |

Test Procedure.

Preparation.

Five volunteers (10 hands) were recruited. A 60 s scrub with non-bactericidal soap followed by a 60 s rinse was performed prior to each experiment.

Contamination.

Hands were contaminated with $1 \times 10^6$ CFU/10 mL non-toxigenic *C. difficile* spores (ATCC 700057).

A modification of the standard hand wash test method, ASTM E1174-06, was used to sample hands. For experiments 4-6, a 30 second rinse after rubbing in the test composition for 30 seconds was performed prior to hand sampling.

Evaluation of Viable *C. difficile* Spores.

Neutralizing buffer was used to sample hands and inactivatetest composition. Quantitative cultures were performed in quadruplicate on BHI agar with horse blood and taurocholate (Anaerobe Systems, Morgan Hill, Calif.). Log geometric mean (LGM) of viable *C. difficile* spores from each assay condition was calculated.

Results.

| Sample | LGM* CFU/10 mL | Standard deviation | p-value (vs. control) |
|---|---|---|---|
| 1 (control) | 4.36 | 0.17 | — |
| 2 (rinse) | 3.31 | 0.30 | <0.001 |
| 3 (wash) | 2.46 | 0.29 | <0.001 |
| 4 | 3.04 | 0.22 | <0.001 |
| 5 | 4.38 | 0.16 | 0.681 |
| 6 | 2.82 | 0.17 | <0.001 |

*log geometric mean ($\log_{10} x$)

Additionally, no skin irritation was noted after any of the experiments.

What is claimed is:

1. A sporicidal composition, comprising:
   water;
   an amount $q_s$ of organic solvent, wherein $q_s$ is about 5% to about 60% w/w; and
   an amount $q_{g1}$ of spore-germinating agent, wherein $q_{gi}$ is about 0.05% to about 5% w/w;
   wherein:
      the organic solvent comprises a glycol, glycerine, a glycol ether, a polyethylene glycol or dimethyl isosorbide; and
      the spore-germinating agent comprises:
         an amount $q_{i1}$ of iodide source, or
         an amount $q_{c1}$ of citrate source, or
         a combination thereof;
         wherein:

$q_{g1} \geq q_{i1} + q_{c1}$; and at least one of $q_{i1}$ and $q_{c1}$ is at least about 0.05% w/w.

2. The sporicidal composition of claim 1, wherein:
   the spore-germinating agent consists essentially of:
      an amount $q_{i1}$ of iodide source, or
      an amount $q_{c1}$ of citrate source, or
      a combination thereof;
      wherein:

$q_{g1} \geq q_{i1} + q_{c1}$; and at least one of $q_{i1}$ and $q_{c1}$ is at least about 0.05% w/w.

3. The sporicidal composition of claim 2, wherein:

$q_{g1} = q_{i1} + q_{c1}$.

4. The sporicidal composition of claim 1, wherein:
$q_{g1}$ is about 0.10% to about 2.3% w/w; and
at least one of $q_{i1}$ and $q_{c1}$ is at least about 0.10% w/w.

5. A sporicidal composition, comprising:
water;
an amount $q_s$ organic solvent, wherein $q_s$ is about 5% to about 60% w/w; and
an amount $q_{g2}$ spore-germinating agent, wherein $q_{g2}$ is about 0.03% to about 3.8% w/w;
wherein:
the organic solvent comprises a glycol, glycerine, a glycol ether, a polyethylene glycol or dimethyl isosorbide; and
the spore-germinating agent comprises:
an amount $q_{i2}$ of iodide, or
an amount $q_{c2}$ of citrate, or
or a combination thereof;
wherein:

$q_{g2} \geq q_{i2} + q_{c2}$; and one or both of (a) and (b):
(a) $q_{i2}$ is about 0.04% to about 3.8% w/w;
(b) $q_{c2}$ is about 0.03% to about 3.2% w/w.

6. The sporicidal composition of claim 5, wherein:
the spore-germinating agent consists essentially of:
an amount $q_{i2}$ of iodide, or
an amount $q_{c2}$ of citrate, or
or a combination thereof;
wherein:

$q_{g2} \geq q_{i2} + q_{c2}$; and one or both of (a) and (b):
(a) $q_{i2}$ is about 0.04% to about 3.8% w/w;
(b) $q_{c2}$ is about 0.03% to about 3.2% w/w.

7. The sporicidal composition of claim 6, wherein:

$q_{g2} = q_{i2} + q_{c2}$.

8. The sporicidal composition of claim 5, wherein:
$q_{g2}$ is about 0.06% to about 1.80% w/w; and
one or both of (a) and (b):
(a) $q_{i2}$ is at least about 0.08% w/w;
(b) $q_{c2}$ is at least about 0.06% w/w.

9. The sporicidal composition of claim 1, wherein the organic solvent comprises glycerine, propylene glycol or butylene glycol.

10. The sporicidal composition of claim 1, wherein the spore-germinating agent consists essentially of an iodide source or a combination of an iodide source and a citrate source.

11. The sporicidal composition of claim 1, wherein the spore-germinating agent consists essentially of a citrate source or a combination of a citrate source and an iodide source.

12. The sporicidal composition of claim 10, wherein the iodide source comprises potassium iodide.

13. The sporicidal composition of claim 11, wherein the citrate source comprises citric acid, sodium citrate monobasic or a hydrate thereof, sodium citrate dibasic or a hydrate thereof, or sodium citrate tribasic or a hydrate thereof.

14. A disinfecting composition, comprising:
the sporicidal composition of claim 1; and
a disinfectant.

15. An antiseptic composition, comprising:
the sporicidal composition of claim 1; and
an antiseptic.

16. A method of reducing the bacterial spore count on a non-living tissue surface, comprising:
applying an effective amount of the composition of claim 1 to the surface;
wherein the spore bacteria comprise bacteria of the genus *Clostridium*.

17. A method of reducing the bacterial spore count on a living tissue surface, comprising:
applying an effective amount of the composition of claim 1 to the surface;
wherein the spore bacteria comprise bacteria of the genus *Clostridium*.

* * * * *